United States Patent [19]

Frick et al.

[11] Patent Number: 5,392,904
[45] Date of Patent: Feb. 28, 1995

[54] MIXING CAPSULE FOR DENTAL COMPOSITIONS

[75] Inventors: Hans-Jörg Frick, Schaan; Peter Kunkel, Triesen, both of Liechtenstein

[73] Assignee: Firma Ivoclar AG, Schaan, Liechtenstein

[21] Appl. No.: 242,591

[22] Filed: May 12, 1994

[30] Foreign Application Priority Data

May 12, 1993 [DE] Germany ............... 4315920

[51] Int. Cl.⁶ ........................................... B65D 25/08
[52] U.S. Cl. .................. 206/219; 206/63.5; 366/602
[58] Field of Search .............. 206/219, 220, 221, 222, 206/63.5; 366/602

[56] References Cited

U.S. PATENT DOCUMENTS

| | | | |
|---|---|---|---|
| 3,073,439 | 1/1963 | Symmonds, Jr. ................. | 206/60 |
| 3,152,693 | 10/1964 | Anderson ...................... | 206/60 |
| 3,637,234 | 1/1972 | Thomas et al. ................. | 280/179 A |
| 4,202,449 | 5/1980 | Bendt .......................... | 206/453 |
| 4,765,479 | 8/1988 | Roberts ........................ | 206/453 |
| 4,858,759 | 8/1989 | Mauthe et al. ................. | 206/219 X |
| 4,938,357 | 7/1990 | Schmidt ........................ | 206/453 |
| 4,941,751 | 7/1990 | Muhlbauer ..................... | 206/222 X |
| 5,026,283 | 6/1991 | Osanai et al. ................. | 206/222 X |
| 5,172,807 | 12/1992 | Dragan et al. ................. | 206/219 |
| 5,297,698 | 3/1994 | Martin ......................... | 206/222 X |

Primary Examiner—Jacob K. Ackun, Jr.
Attorney, Agent, or Firm—Robert W. Becker & Associates

[57] ABSTRACT

A capsule for dental compositions has a mixing chamber for mixing a dental composition that contains a first component of the dental composition and has a bottom with an outlet opening for the dental composition. A piston is positioned in an initial position at an upper end of the mixing chamber. The piston has at least one recess and an inner chamber containing a second component of the dental composition. The inner chamber has a bottom in the form of a temporary seal. A plunger is positioned in an initial position at an upper end of the inner chamber of the piston. Upon depressing the plunger, the temporary seal is broken to introduce the second component into the mixing chamber. A manually removable U-shaped locking member has two legs and a connecting bar connecting the legs wherein the connecting bar is elongate in a direction pointing away from the legs to form a grip portion. The locking member engages with the legs the at least one outer recess of the piston for locking the piston relative to the mixing chamber. Upon removal of the locking member the piston is slidable toward the outlet opening for releasing the dental composition.

19 Claims, 2 Drawing Sheets

MIXING CAPSULE FOR DENTAL COMPOSITIONS

BACKGROUND OF THE INVENTION

The present invention relates to a mixing capsule for dental compositions having a mixing chamber in which a piston is slidably guided whereby within the piston a plunger is slidably arranged and wherein the mixing chamber is provided with an outlet opening via which the dental composition can be forced out of the mixing chamber.

From German Offenlegungsschrift 20 60 262 such a mixing capsule for dental compositions is known. Such a mixing capsule is provided with a hollow piston in which a plunger is guided whereby the hollow piston, in general, contains a liquid substance which is separated from a powdery substance by a foil that is capable of being torn whereby the powdery substance is contained in the mixing chamber. By depressing the plunger the foil is torn and the generally liquid substance is pressed out of the hollow piston and also introduced also into the mixing chamber so that the substances can be mixed within an automatic oscillating mixing device, for example, a so-called amalgam mixer.

It is important to realize that the piston upon depressing the plunger should not also be forced into the mixing chamber, not even to the smallest extent. Otherwise there is the danger that the mixing chamber volume is decreased such that a complete mixing of the components, for example, of a fastening cement, is possible only to a limited extent and that the cement will suffer an unacceptable quality loss.

For solving this problem it is suggested in German Offenlegungsschrift 20 60 626 to provide the piston with lateral projections whereby the depression of the plunger is carried out such that the projections provide a kind of counter grip which can be held with two fingers while the plunger is provided with a thumb rest.

This solution in principle is favorable since this arrangement corresponds to the natural hand position used for depressing a syringe. Since the mixing chamber itself also has corresponding projections for emptying there is the risk that when an operator is careless or is in training for using this apparatus, that accidentally the projections of the mixing chamber are used instead of the projections of the hollow piston as counter grips, which mistake may even remain undetected.

In addition, it is also known, for example, from German Offenlegungsschrift 20 24 331 and German Offenlegungsschrift 19 39 316, to support a hollow piston at the mixing chamber with a support or spring ring. The spring ring is removed with a conventional spring ring remover before removing the finish-mixed tooth cement or amalgam so that the hollow piston is freely displaceable and can be depressed.

In this solution it is disadvantageous that the piston together with the liquid contained therein is not secured in an optimal manner. The plunger is provided with sealing lips relative to the hollow piston so that no liquid can emerge. However, when the plunger is already depressed, depending on how the device is handled, a relative movement between piston and mixing chamber may occur, especially since the entire capsule is greatly accelerated within the amalgam mixer, and even when this relative movement is relatively small, it may happen that liquid leaks into the gap between the mixing chamber and the piston which would result in undesirable contamination.

A plurality of other mixing capsules has also been suggested whereby the capsule according to German Offenlegungsschrift 37 18 326 shall be mentioned as an example. In this mixing capsule a piston is always completely received within the mixing chamber. From the exterior it is not easily detectable in which state the mixing capsule is at the moment, whether, for example, the foil container containing the liquid is already broken or whether the piston is at this point simply depressed to some extent. The capsule is only secure when it is positioned in an actuating device. However, when in practice a plurality of capsules needs to be prepared, it is required to purchase a plurality of actuating devices. Furthermore, there is a risk that, when the capsule is inserted in a conventional amalgam mixer after depressing the plunger, the piston is moved inwardly to a certain extent so that the gap between piston and plunger reaches the area of the engagement opening which would also lead to contamination.

It is therefore an object of the present invention to provide a mixing capsule of the aforementioned kind which in practice can be operated securely and prevents contamination without the need for replacement of conventional automatic oscillating devices with new constructions.

BRIEF DESCRIPTION OF THE DRAWINGS

This object, and other objects and advantages of the present invention, will appear more clearly from the following specification in conjunction with the accompanying drawings, in which.

SUMMARY OF THE INVENTION

Figure 3:
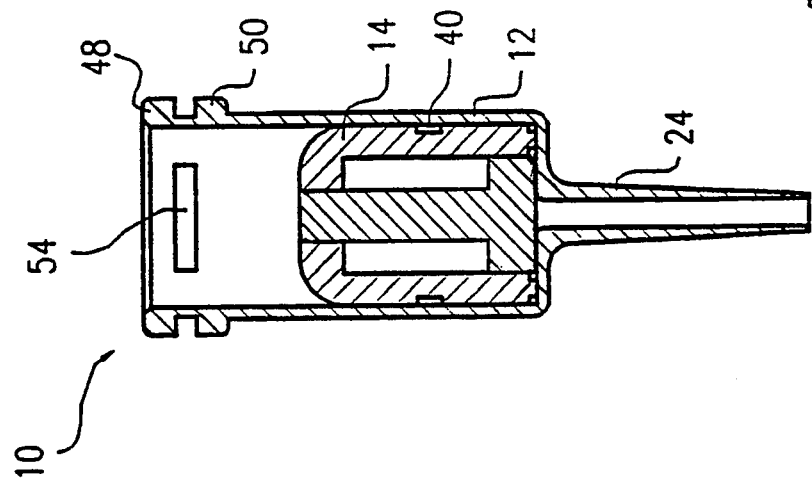
FIG. 3 shows the embodiment of the mixing capsule of FIG. 2 whereby the mixing capsule has been emptied.

The mixing capsule for a dental composition according to the present invention is primarily characterized by:

A mixing chamber for mixing a dental composition, the mixing chamber containing a first component of the dental composition and having a bottom with an outlet opening for the dental composition;

A piston positioned in an initial position at an upper end of the mixing chamber;

The piston having at least one recess and an inner chamber containing a second component of the dental composition, the inner chamber having a bottom in the form of a temporary seal;

A plunger positioned in an initial position at an upper end of the inner chamber of the piston, wherein upon depressing the plunger the temporary seal is broken to introduce the second component into the mixing chamber;

A manually removable U-shaped locking member having two legs, and a connecting bar connecting the two legs wherein the connecting bar is elongate in a direction pointing away from the legs to form a grip portion, the locking member engaging with the legs the at least one recess of the piston for locking the piston relative to the mixing chamber; and Wherein upon removal of the locking member the piston is slidable toward the outlet opening for releasing the dental composition.

Advantageously, the locking member is insertable into the at least one recess and is a part separate from the piston and the mixing chamber.

Preferably, the at least one recess is an annular groove and the locking member is disposable.

Expediently, the at least one recess has a first step at an outer surface of the piston with a downwardly oriented shoulder facing the outlet opening. Preferably, the at least one recess has a second step at the outer surface of the piston with an upwardly oriented shoulder facing away from the outlet opening.

Advantageously, the locking member engages the piston on two diametrically opposite locations at a step of the at least one recess.

Alternatively, the locking member engages the piston on two locations that are staggered relative to one another.

Preferably, the mixing chamber has a through opening for allowing the locking member to penetrate.

In a preferred embodiment of the present invention, the mixing chamber has an upwardly facing support surface for supporting the locking member.

In another embodiment of the present invention, the mixing chamber has an outer circumferential annular groove for receiving the two legs of the locking member. Advantageously, the outer circumferential annular groove is formed by two outwardly projecting annular beads between which the locking member is held, wherein a bottom of the circumferential annular groove has two perforations at diametrically opposite locations and wherein the two legs of the locking member project through the perforations. Preferably, the two legs of the locking member are elastically biased toward one another so as to catch in the at least one recess.

In a preferred embodiment of the present invention, the piston is bell-shaped and has a top portion in which top portion a rod of the plunger is guided. Advantageously, the length of the plunger including the rod is equal to the length of the piston so that the plunger is completely insertable into the piston.

Expediently, the length of the mixing chamber is substantially greater than the length of the piston so that the piston is completely insertable into the mixing chamber.

Preferably, the dimensions and materials of the piston and the mixing chamber and the dimensions and materials of the plunger and the piston are selected relative to one another such that friction between the piston and the mixing chamber is smaller than friction between the plunger and the piston.

Advantageously, the plunger comprises a rod having a smooth surface and being thin and without a grip portion so that the plunger is removable from the piston only with a tool. Preferably, the plunger is of a bright, conspicuous color.

Expediently, the mixing capsule further comprises a closure rod for closing the outlet opening in an airtight manner. Friction of the plunger in the piston upon displacement should be greater than the compression force for air present within the mixing chamber.

Surprisingly, with the inventive manually removable locking member the inventive mixing capsule is more reliable in operation within conventional oscillating devices whereby even with respect to the operational handling sequences a clear indication of the state of the mixing capsule is ensured that prevents operational errors. Since the locking member engages a special recess within the hollow piston, the position of the piston is always arrested and clearly identifiable so that the position of the piston upon insertion into the automatic oscillating device is always clearly detectable. On the other hand, the arresting action of the locking member prevents reliably a minimal movement of the piston counter to the considerable acceleration forces within the oscillating device so that liquid that is not yet completely mixed liquid cannot exit. Furthermore, a premature displacement of the piston during the mixing process is prevented whereby after the mixing action the fixation of the piston is manually releasable in a simple manner.

Furthermore, the inventive mixing capsule is very inexpensive since the locking member is embodied as a simple disposable and insertable separate part that is not fixedly connected with either the mixing chamber or the pressing device. Despite its multi-functionality it may be embodied as a very light component so that it does not reduce or reduce only to a small extent the oscillation frequency of the oscillating device.

It is especially advantageous that the piston together with the plunger including the liquid enclosed by a foil can be manufactured as a complete unit and that this unit can be inserted into the mixing chamber after the mixing chamber has been filled with the required powder and after a closure rod has been inserted. As soon as the inventive locking member is inserted and/or interlocked, a secure and contamination-protected unit results in which the components to be mixed for the application are securely separated.

In this context it is to be understood that the friction between the plunger and the piston is to be selected so great that an accidental depression of the plunger is impossible. This can be achieved in a manner known per se by providing a corresponding fit between the parts.

Due to a bell-shaped embodiment of the piston the liquid mixture component as well as the plunger are protected by a massive piston wall and a massive piston top.

Various embodiments of the invention are possible in order to provide the required form-locking between the mixing chamber and the piston via the inventive locking member. For example, the piston may be provided outwardly with a shoulder that faces downwardly, i.e., toward the outlet opening, and can thus counteract an undesired insertion of the piston into the mixing chamber. On the other hand, it is possible to provide an upwardly facing shoulder, i.e., facing the free end of the plunger, to thereby prevent the accidental removal or slipping-out of the piston out of the mixing chamber. Accordingly, it is especially favorable when the two shoulders are arranged adjacent to one another in the axial direction and are provided at a recess which is recessed relative to the piston surface, i.e., are thus provided at a groove or depression, whereby it is preferred that this recess is not a through opening and thus does not penetrate the piston wall.

According to a further preferred embodiment the locking member is supported at two oppositely arranged sides. With the thus symmetrically acting forces no canting will occur when the piston is pressurized against the effect of the locking member. It is understood that the support must not be provided at the same height at the oppositely arranged sides; it is instead also possible, if desired, to provide a height-wise staggering.

Preferably, the locking member is provided with a grip portion which allows for a fast and reliably identifiable removal of the locking member. Accordingly, there is no delay with respect to providing the finish-mixed tooth cement or other dental composition, and accordingly, the available mixing time is not reduced.

Preferably, the locking member is shaped to match the piston and extends in a slot of the mixing chamber. This embodiment allows a minimal material requirement for the locking member despite a secure stabilization. It is understood that the locking member and the corresponding recesses or depressions within the piston, which is preferably in the form of a hollow piston, are matched relative to one another.

It is also understood that in the interior of the hollow piston as well as in the interior of the mixing chamber which is covered by the piston there must be sufficient free space in order to receive the maximum amount of components to be mixed whereby the free space in the mixing chamber must be dimensioned to receive in addition to the powdery material also the liquid component and it must be ensured that for the mixing process within the oscillating fork mixer sufficient free space for the mixing operation is provided.

According to a further preferred embodiment an activating protection is provided which is in the form of an envelope foil which covers the plunger. The envelope foil, which is, for example, transparent or translucent, allows to detect whether the plunger is slightly depressed, for which purpose it may be made of elastic material such as silicone rubber. According to a further embodiment the activating protective foil has a brittle lacquer-type costing. An activation of the plunger is then impossible without destroying the coating so that the intactness of the coating indicates that the mixing capsule all together is still unused.

However, it is especially favorable that independent of the activating protective foil the non-depressed plunger already signals the readiness of the capsule. In this context it is especially advantageous that the plunger within the piston is relatively difficult to displace; furthermore, after it has been introduced, it can no longer be removed without tools. The plunger therefore serves at the same time as a signal for the readiness of the capsule without the need for increasing further the friction between the piston and the mixing chamber based on the increased friction between the plunger and the piston which would make questionable the usability within a conventional dispenser.

DESCRIPTION OF PREFERRED EMBODIMENTS

The present invention will now be described in detail with the aid of several specific embodiments utilizing FIGS. 1 through 5.

Figure 1:
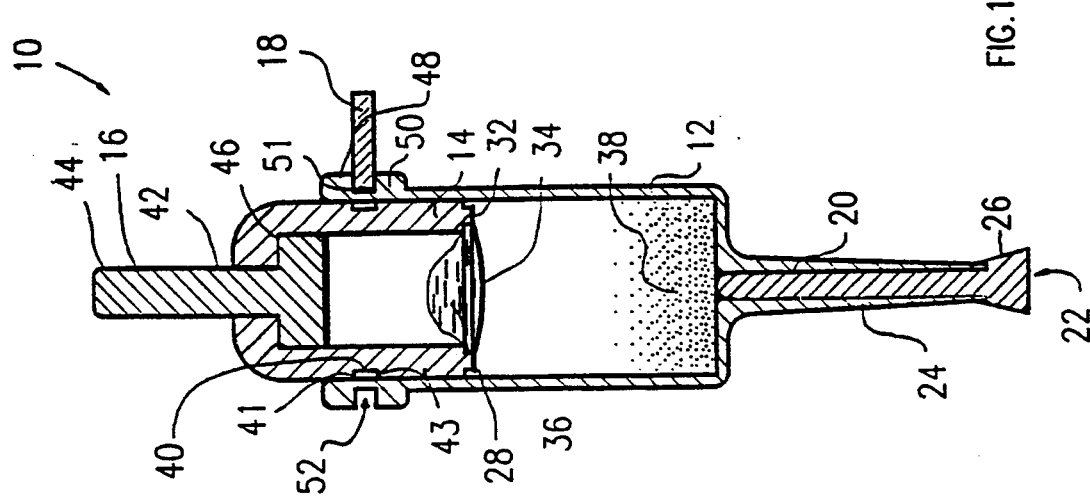
FIG. 1 shows a sectional view of the inventive mixing capsule in a first embodiment in the assembled state before activation.
Figure 5:
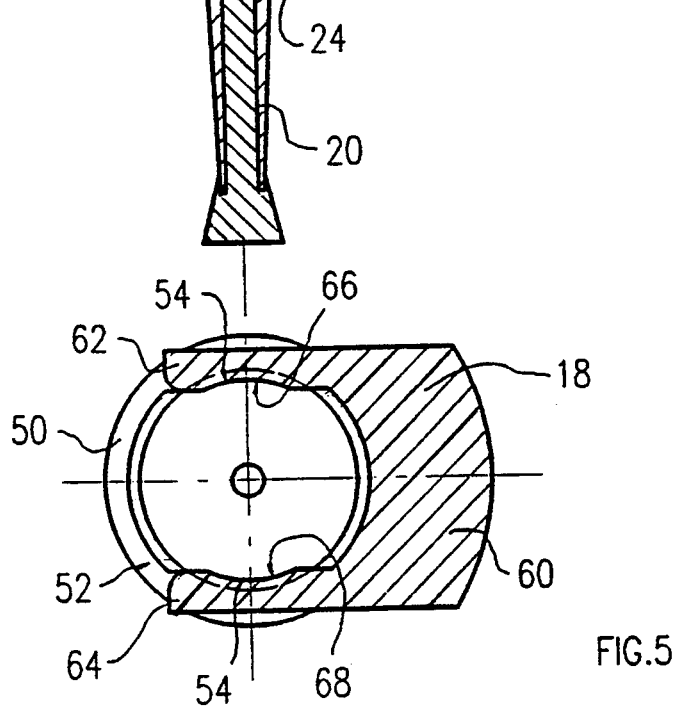
FIG. 5 shows a section along the line V—V of FIG. 4.

A mixing capsule 10 is represented in one embodiment in FIG. 1 in a sectional view. The mixing capsule 10 has a mixing chamber 12, a piston 14 which is in the form of a hollow piston, and a plunger 16. Inventively, the piston 14 is arrested at the mixing chamber 12 with a locking member 18 the embodiment of which is represented in FIG. 5.

The mixing chamber 12 is closed at its lower end with a closure rod 20 which is to be removed before ejecting the finished mixture.

The mixing chamber 12 for this purpose tapers off into an outlet opening 22 that in the downward direction is provided with an ejecting channel 24 in the manner of a syringe, respectively, a canula. The ejecting channel 24 has a substantially uniform cross-section over its entire length while its outer diameter tapers in direction to the tip.

The closure rod 20 has also substantially a uniform outer diameter over its entire length, whereby the dimensioning of the closure rod 20 and the ejecting channel 24 is selected such that in the inserted state the closure rod 20 provides for a secure and airtight closure.

The closure rod 20 ends at its lower end in a protrusion 26 that is provided with an axially oriented annular groove into which the tip of the ejecting channel 24 is inserted in order to provide an additional line sealing. Furthermore, the protrusion 26 serves has a handle for the removal of the closure rod 20 before the finished tooth cement is to be ejected.

In the state represented in FIG. 1 the flowable, especially liquid substance 28, for example, phosphoric tooth cement liquid, is contained in the piston 14. The annular edge 32 of the foil 34 (temporary seal) is glued or fused to a downwardly projecting annular projection 36 of the hollow piston 14. In the radial direction the annular projection 36 is recessed inwardly as well as outwardly relative to the wall of the hollow piston 14. This ensures a secure connection independent of the sliding of the hollow piston 14 within the mixing chamber 12.

Figure 2:
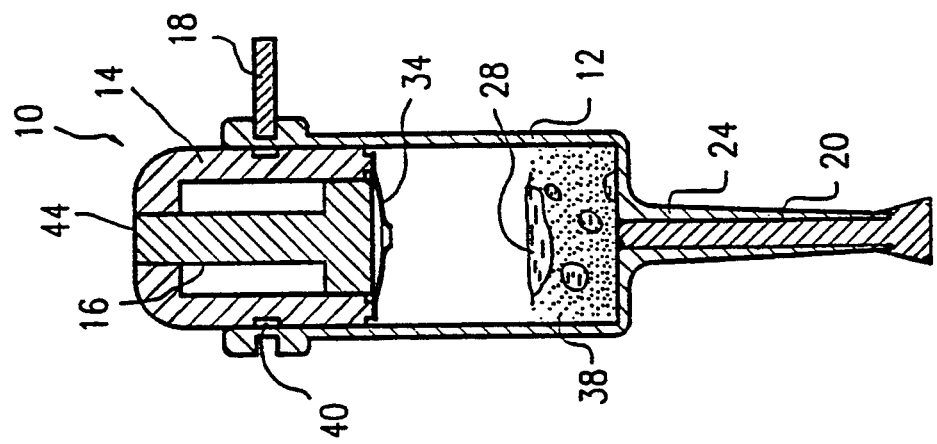
FIG. 2 shows a slightly modified embodiment of the mixing capsule according to FIG. 1 whereby the mixing capsule is in its activated state.

The foil 34 acts as a temporary seal and is provided in a manner known per se with a predetermined breaking point. The strength of this predetermined breaking point is substantially smaller than the strength of the glue or fuse connection between the annular projection 36 and the edge 32 so that during activation according to FIG. 2, i.e., during depressing the plunger 16, the foil 34 will reliably rupture as represented in FIG. 2 so that the contents will flow into the mixing chamber 12.

The mixing chamber 12 in the initial state according to FIG. 1 receives a powdery substance 38 such as silicate cement powder, zinc oxide etc. The hollow chamber which forms the mixing chamber 12 is dimensioned such that even at the maximum present filling volume more than half of the hollow chamber remains unfilled so that later on a good mixing is possible.

The hollow piston 14 is substantially bell-shaped and provided with a relatively massive wall thickness as well as with a massive upwardly positioned bottom. In the shown embodiment a recess in the form of an annular groove 40 is located at substantially half the height of the piston 14 and is designed to receive the locking member 18. While in the shown embodiment the annular groove 40 is U-shaped it is, for example, also possible to provide a V-shaped embodiment whereby it is important that axial play between the locking member 18 and the annular groove 40 is as little as possible, but that a secure interlocking of the locking member 18 and the annular groove 40 is still possible. The annular groove 40 thus provides for the locking member 18 at the upper end a downwardly facing shoulder 41 and at the lower end an upwardly facing shoulder 43.

The hollow piston 14 is provided with a through opening 42 for the plunger 16 with which its diameter is adapted to the diameter of the rod 44 of the plunger.

The inner diameter of the hollow piston 14 is adapted to the diameter of the plunger piston 46 arranged therein. The plunger 16 has a length that is also adapted to the length of the hollow piston 14, as can be seen especially in FIG. 2, so that after complete insertion of the plunger 16 the liquid substance 28 is securely forced from the hollow piston 14.

The locking member 18 is held at the upper end of the mixing chamber 12 between two annular beads 48 and 50. The annular beads 48 and 50 define between them an outer circumferential annular groove 52 having a bottom that at two oppositely arranged locations, as can be seen especially in FIG. 5, is provided with perforations so that the locking member 18 is in engagement with the annular groove 40. The lower annular bead 50 is provided with an upwardly oriented support surface 51 on which the locking member 18 is supported.

FIG. 2 shows the activated state of the mixing capsule 10 represented in FIG. 1. Same reference numerals indicate same parts in the following figures. In this state, the plunger 16 is completely inserted so that the upper end of the rod 44 of the plunger 16 is flush with the upper end of the hollow piston 14. The foil 34 has ruptured and the liquid substance 28 is released so that it is already somewhat mixed with the powdery substance 38 in the mixing chamber 12 or at least is in contact with it. The locking member 18 remains in the annular groove 40 and the closure rod 20 remains inserted in the ejecting channel 24. In this state the inventive mixing capsule 10 is placed into a mixing device, not represented, which due to its oscillating movements provides for an intensive mixing of the solid and liquid substances for producing an amalgam mixture or a tooth cement etc.

After lapse of the mixing time, the inventive mixing capsule 10 is expediently introduced into a non-represented dispenser. Before doing so, the locking member 18 as well as the closure rod 20 are manually removed and disposed of. The finished mixture can then be ejected whereby the completely empty state is represented in FIG. 3. In this state the piston 14 together with the enclosed plunger 16 is completely inserted into the mixing chamber 12 and rests at its lower end.

FIG. 3 shows that the bottom of the groove 52 has a slot-shaped opening 54 that is provided for the penetration of the locking member 18.

Figure 4:
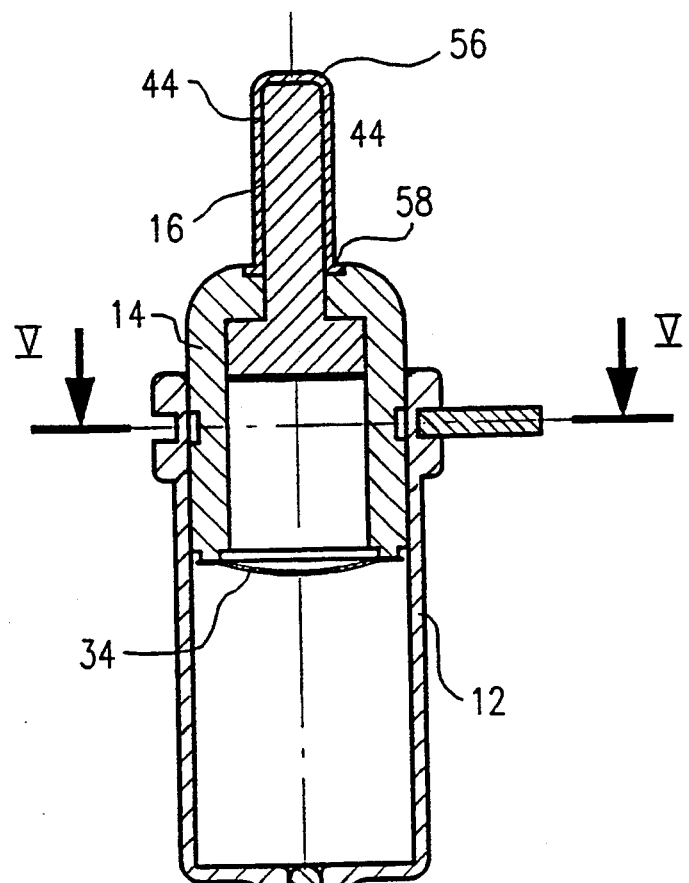
FIG. 4 shows a section of the embodiment of the mixing capsule of FIG. 2 in the non-activated state.

In FIG. 4 a modified embodiment of the inventive mixing capsule is represented. This embodiment has an activating protective foil 56 which in the initial mounted state extends completely over the projecting part of the rod 44 of the plunger 16. When the activating protective foil 54 is unharmed, it can be deduced that the foil 34 is also intact so that the mixing capsule 10 is ready for use. The activating protective foil 56 at its lower end is connected to the upper end of the hollow piston 14, for example, by gluing or fusing, whereby for this purpose at this location a corresponding depression is provided.

In FIG. 5 neither the dental composition 28 nor the dental composition 38 are represented. Also, only the lower foil 34 is indicated. In principle, it is also possible to use a foil envelope known per se which however in practice can never be completely emptied.

FIG. 5 shows a section along the line V—V of FIG. 4. Here it is shown that the locking member 18 is provided with a grip portion 60 which is plate-shaped. In general, the locking member 18 is substantially U-shaped whereby two legs 62 and 64 serve for engaging the annular groove 40. For this purpose, the legs 62 and 64 penetrate respectively the openings 54 in the outer circumferential annular groove 52 between the annular beads 48 and 50 of the mixing chamber 12. The openings 54 are positioned symmetrically opposite one another and the legs 62 and 64 are provided with a rounded portion 66 and 68, respectively, the radius of which is matched to the radius of the bottom of the annular groove 40. With these rounded portions the locking member 18 interlocks at the hollow piston 14 so that it is secured in a safe manner and can be removed only by pulling manually at the grip portion 60.

It is preferred that the grip portion 60 also ends with a radius so that, on the one hand, a secure grip is possible and, on the other hand, the locking member 18 conforms as closely as possible to the shape of the mixing capsule 10. The weight of the locking member 18 is neglectable relative to the weight of the mixing capsule 10.

The present invention is, of course, in no way restricted to the specific disclosure of the specification and drawings, but also encompasses any modifications within the scope of the appended claims.

What we claim is:

1. A capsule for a dental composition, said capsule comprising:
    a mixing chamber for mixing a dental composition, said mixing chamber containing a first component of the dental composition and having a bottom with an outlet opening for the dental composition;
    a piston positioned in an initial position at an upper end of said mixing chamber;
    said piston having at least one recess and an inner chamber containing a second component of the dental composition, said inner chamber having a bottom in the form of a temporary seal;
    a plunger positioned in an initial position at an upper end of said inner chamber of said piston, wherein upon depressing said plunger said temporary seal is broken to introduce said second component into the mixing chamber;
    a manually removable U-shaped locking member having two legs and a connecting bar connecting said two legs, wherein said connecting bar is elongate in a direction pointing away from said legs to form a grip portion, said locking member engaging with said legs said at least one recess of said piston for locking said piston relative to said mixing chamber; and
    wherein upon removal of said locking member said piston is slidable toward said outlet opening for releasing the dental composition.

2. A capsule according to claim 1, wherein said locking member is insertable into said at least one recess and is a part separate from said piston and said mixing chamber.

3. A capsule according to claim 2, wherein said at least one recess is an annular groove and wherein said locking member is disposable.

4. A capsule according to claim 1, wherein said at least one recess has a first step at an outer surface of said piston with a downwardly oriented shoulder facing said outlet opening.

5. A capsule according to claim 4, wherein said at least one recess has a second step at the outer surface of said piston with an upwardly oriented shoulder facing away from said outlet opening.

6. A capsule according to claim 1, wherein said locking member engages said piston on two diametrically opposite locations at a step of said at least one recess.

7. A capsule according to claim 1, wherein said locking member engages said piston on two locations that are staggered relative to one another.

8. A capsule according to claim 1, wherein said mixing chamber has a through opening for allowing said locking member to penetrate.

9. A capsule according to claim 1, wherein said mixing chamber has an upwardly facing support surface for supporting said locking member.

10. A capsule according to claim 1, wherein said mixing chamber has an outer circumferential annular groove for receiving said two legs of said locking member.

11. A capsule according to claim 10, wherein said outer circumferential annular groove is formed by two outwardly projecting annular beads between which said locking member is held, wherein a bottom of said circumferential annular groove has two perforation at diametrically opposite locations and wherein said two legs of said locking member project through said perforations.

12. A capsule according to claim 1, wherein said two legs of said locking member are elastically biased toward one another so as to catch in said at least one recess.

13. A capsule according to claim 1, wherein said piston is bell-shaped and has a top portion in which top portion a rod of said plunger is guided.

14. A capsule according to claim 13, wherein a length of said plunger including said rod is equal to a length of said piston so that said plunger is completely insertable into said piston.

15. A capsule according to claim 1, wherein a length of said mixing chamber is substantially greater than a length of said piston so that said piston is completely insertable into said mixing chamber.

16. A capsule according to claim 1, wherein the dimensions and materials of said piston and said mixing chamber and the dimensions and materials of said plunger and said piston are selected relative to one another such that friction between said piston and said mixing chamber is smaller than friction between said plunger and said piston.

17. A capsule according to claim 1, wherein said plunger comprises a rod having a smooth surface and being thin and without a grip portion so that said plunger is removable from said piston only with a tool.

18. A capsule according to claim 17, wherein said plunger is of a bright, conspicuous color.

19. A capsule according to claim 1, further comprising a closure rod for closing said outlet opening in an airtight manner, wherein a friction of said plunger in said piston upon displacement is greater than the compression force for air present within said mixing chamber.

* * * * *